United States Patent [19]

Chen et al.

[11] 4,329,876
[45] May 18, 1982

[54] METHOD AND APPARATUS FOR ACOUSTIC SCANNING USING BULK WAVE SCATTERING OF BULK WAVES BY AN ACOUSTIC GRATING

[75] Inventors: Wen-Hsien Chen, Ta-hsi, Taiwan; Eric G. Lean, Chappaqua, N.Y.

[73] Assignee: International Business Machines Corporation, Armonk, N.Y.

[21] Appl. No.: 156,226

[22] Filed: Jun. 3, 1980
(Under 37 CFR 1.47)

[51] Int. Cl.³ .......................................... G01N 29/04
[52] U.S. Cl. ...................................... 73/618; 73/627; 73/642
[58] Field of Search ................. 73/618, 620, 627, 632, 73/642; 310/322, 334, 335, 336, 313 R; 367/103

[56] References Cited

U.S. PATENT DOCUMENTS 3,283,264  11/1966  Papadakis ........................... 310/322
3,400,341   9/1968  Sittig ............................... 310/313 R
4,011,747   3/1977  Shaw ................................. 73/642

Primary Examiner—Stephen A. Kreitman
Attorney, Agent, or Firm—Ronald L. Drumheller

[57] ABSTRACT

Electronically focused and automatically scanning acoustic bulk waves are produced by scattering chirp acoustic bulk waves at grazing incidence from an acoustic grating. The same apparatus may be used in reverse to convert diverging acoustic bulk waves produced by a focused beam into chirp acoustic bulk waves. A pulse compression filter then converts the chirp waves into signals describing the source.

31 Claims, 3 Drawing Figures

METHOD AND APPARATUS FOR ACOUSTIC SCANNING USING BULK WAVE SCATTERING OF BULK WAVES BY AN ACOUSTIC GRATING

TECHNICAL FIELD

The invention relates to apparatus and a method for generating scanning focused acoustic bulk waves and for converting scanning focused acoustic bulk waves into electrical signals. It may be used to scan an object with focused acoustic bulk waves and to record an acoustic image. Acoustic scanning is used, for example, to non-destructively detect flaws in materials, to produce visual images of internal human organs, and to produce underwater images (sonar).

BACKGROUND ART

One disadvantage of prior art acoustic scanning systems has been a lack of capability of such systems to be operated effectively at very high frequencies. A very high frequency (small wavelength) is desirable because the smallest beam cross-section dimension which can be theoretically attained is proportionally related to the wavelength. Image resolution is limited by the size of this dimension.

Prior art U.S. Pat. No. 4,011,747 generates scanning focused acoustic bulk waves by launching chirp surface acoustic waves along a surface of a solid medium and scattering the propagating surface waves into bulk waves using an acoustic grating on the surface. The scattered acoustic bulk waves are automatically focused as a result of the chirp and scan at substantially the same speed as the surface acoustic waves propagate.

One disadvantage of this prior art arrangement is that the propagating surface waves gradually lose amplitude as they travel across the grating, which results in a scanning acoustic wave which loses amplitude during a scan. In theory, this effect may be compensated by using a grating with grooves of gradually increasing depth. However, such gratings are difficult and expensive to fabricate.

Another disadvantage is that the high frequency performance of this device is compromised by undesirable characteristics of the materials available for the solid medium, which must simultaneously allow both efficient generation and low loss propagation of surface acoustic waves at high frequencies. Materials which allow reasonably efficient generation and propagation of surface acoustic waves at high frequencies are piezoelectric. Unfortunately these materials are anisotropic, so that the ability to focus an acoustic bulk wave is adversely affected. Since the chief reason for using a higher frequency is to reduce one or both of the cross-section dimensions of the acoustic bulk beam, any loss in ability to focus reduces or eliminates the advantage.

Piezoelectric materials also have a much higher surface acoustic wave propagation velocity than some non-piezoelectric materials. All else being equal, this results in a larger minimum dimension for the beam. The frequency must be raised still more to compensate for the higher propagation velocity. Since the beam scanning speed is substantially equal to the surface wave propagation velocity, a higher propagation velocity also increases some of the performance requirements for electronic components.

Use of a piezoelectric solid medium in the prior are device has further disadvantages relating to impedance matching. The acoustic bulk beam must leave the solid medium in order to reach a target. The high characteristic acoustic impedance of piezoelectric materials results in very great amplitude losses and reflections at the material interfaces unless a plurality of special impedance matching layers are used.

Surface acoustic wave propagation is very sensitive to surface boundary conditions. Therefore, the acoustic grating surface in the prior art device cannot be contaminated or placed in contact with any foreign body or substance, which is a further disadvantage.

It is the primary object of this invention to provide apparatus and a method for generating focused acoustic bulk waves which overcome the disadvantages and limitations of the described prior art.

One object is to generate focused acoustic bulk waves at higher acoustic frequencies.

Another object is to generate scanning focused acoustic bulk waves using a uniform depth acoustic grating and not have the focused acoustic bulk waves lose amplitude during a scan.

It is also an object to generate scanning focused acoustic bulk waves at very high frequencies without using piezoelectric or other anisotropic materials.

A further object is to more efficiently generate scanning focused acoustic bulk waves, more efficiently propagate them, and more efficiently transfer them into liquid media such as water.

Still another object is to avoid use of surface acoustic waves and acoustic gratings which interact with surface acoustic waves so that there will be no contamination problem or need to avoid contact with any of the device surfaces.

These and further objects are achieved by the invention.

DISCLOSURE OF INVENTION

Electronically focused and automatically scanning acoustic bulk waves are produced by scattering chirp acoustic bulk waves at grazing incidence from an acoustic grating. The chirp acoustic waves are launched by a bulk wave transducer into a propagation medium and intersect at a grazing angle an acoustic grating comprising an array of obstacles. Acoustic bulk waves scattering from the array of obstacles converge into a focused beam which scans at the propagation speed of the chirp acoustic bulk waves multiplied by the cosine of the grazing angle. The focused beam may be formed by acoustic bulk waves which are transmitted through the acoustic grating or by acoustic bulk waves which are reflected from the acoustic grating.

The same apparatus may be used in reverse to convert diverging acoustic bulk waves produced by a focused beam into chirp acoustic bulk waves. A pulse compression filter then converts the chirp waves into signals describing the source.

BEST MODE FOR CARRYING OUT THE INVENTION

Figure 1:
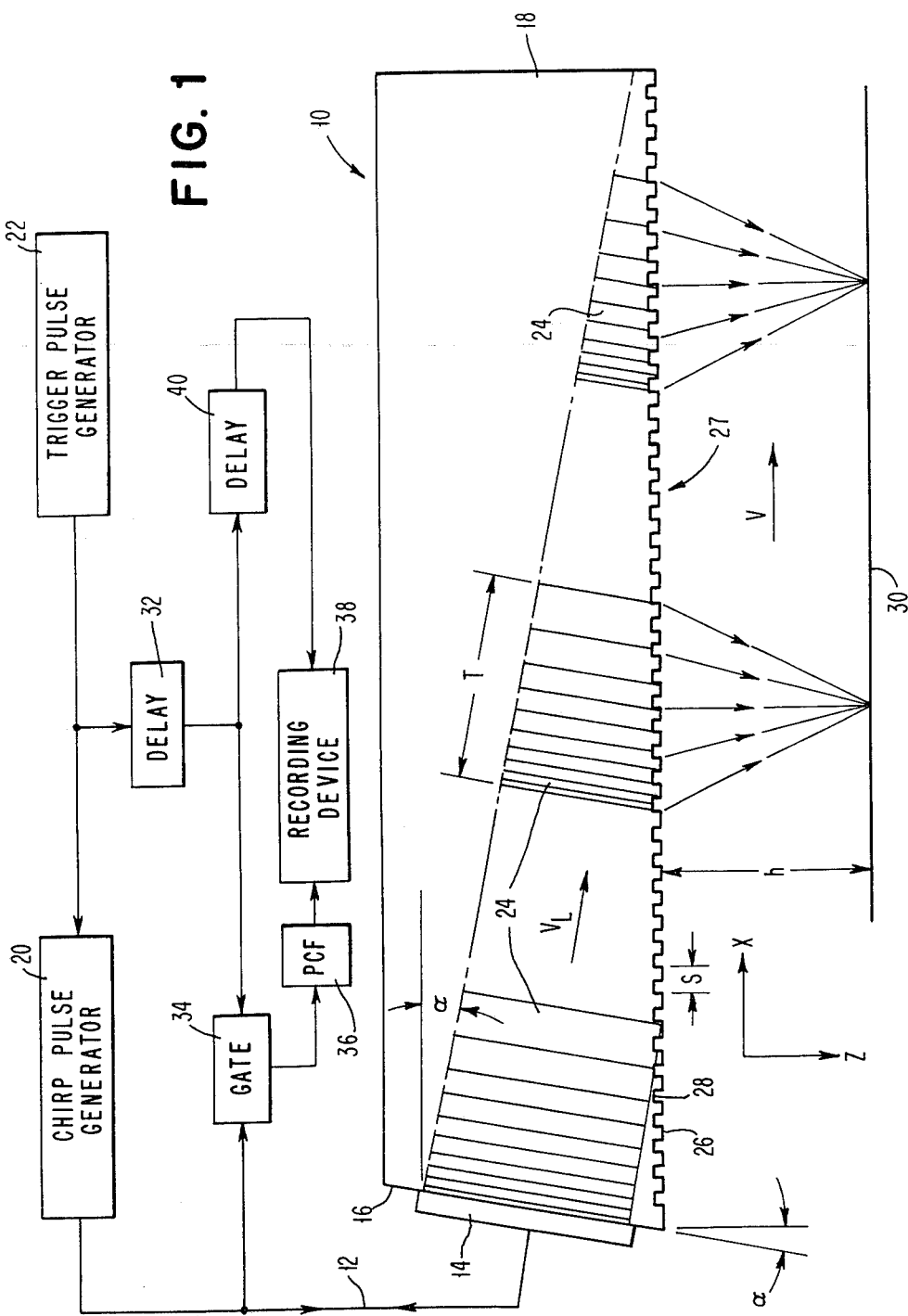
FIG. 1 is a side cross-sectional view of an acoustic scanning apparatus in accordance with the present invention and a block diagram of an electronic system for use with an acoustic scanning apparatus.

Referring now to the Figures, where like reference numerals indicate corresponding parts, reference numeral 10 generally refers to acoustic scanning apparatus in accordance with the present invention. As will become more apparent as the description proceeds, acoustic scanning apparatus 10 may be used in a transmitter mode of operation for generating focused acoustic bulk waves which automatically scan across a field and may be used in inverse fashion in a receiver mode of operation for converting acoustic bulk waves diverging from a focus into electrical signals. When both modes of operation are used sequentially, an acoustic image of an object may be recorded.

A conventional chirp pulse is produced on line 12 and drives an acoustic bulk wave transducer 14 which is mounted on surface 16 of substrate 18. Transducer 14 may be any type of acoustic bulk wave transducer and substrate 18 may be any propagation medium which is sufficiently elastic to efficiently propagate bulk acoustic waves within the frequency range of operation. Propagation medium 18 need not even be a solid material. A broadband indium bonded LiNbO$_3$-on-fused quartz transducer and a fused quartz substrate is preferred. The chirp pulse on line 12 is produced by a conventional chirp pulse generator 20 which is controlled by a trigger pulse generator 22, both of which are commercially available.

A chirp pulse is a constant amplitude short time duration pulse with a linear frequency modulation. After conversion to an acoustic bulk wave pulse by transducer 14, the chirp pulse is represented in the Figures by a series of grouped lines 24 having a variation of spacing. The spacing between lines generally represents the changing wavelength of the acoustic waves constituting the chirp pulse.

Bulk wave chirp pulses are launched by transducer 14 and propagate in a direction perpendicular to surface 16 which is oriented at an acute angle with respect to surface 26 of substrate 18 so that the bulk wave chirp pulses intersect surface 26 at a suitably small angle which will hereinafter be called a grazing angle. An array 27 of perturbations or obstacles 28 forming an acoustic diffraction grating are located along surface 26. Any known grating structure may be used. Perturbations may be formed, for example, by mounting strips of a material on the surface or by forming grooves (as shown). Grooves may have various cross sections. Rectangular and triangular cross sections are examples.

The bulk wave chirp pulses are directed at a grazing angle $\alpha$ to the grating 27 so that they intersect the grating over a greater distance than the spatial period T of the bulk wave chirp pulse. As a result, the pulse interacts with only a portion of the grating at any one instant and the interacting region of the grating gradually changes as the pulse propagates to the right. FIG. 1 shows three separate acoustic chirp pulses or in the alternative represents the same chirp pulse at three different instants of time as it propagates to the right. It should be noted that a constantly changing region of the bulk wave pulse is interacting with the grating as the bulk wave pulse propagates to the right. As a result, the amplitude of the interacting region of the pulse is substantially constant over the scan.

Figure 2:
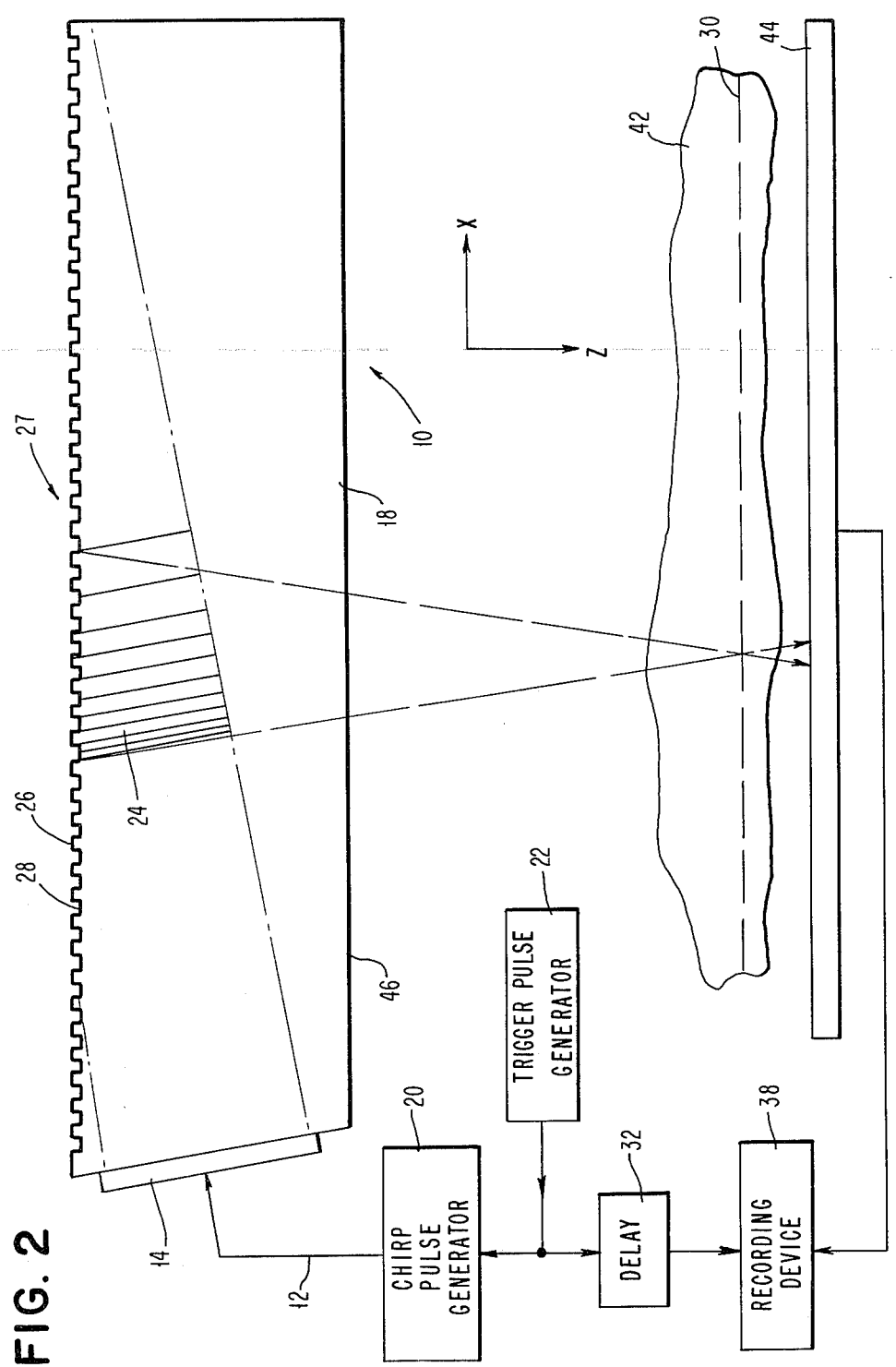
FIG. 2 is a side cross-sectional view of another acoustic scanning apparatus in accordance with the present invention and a block diagram of another electronic system for use with an acoustic scanning apparatus.

The acoustic bulk wave chirp pulses are coherently scattered from the grating 27. FIG. 1 illustrates a transmission grating where the scattered bulk waves of interest are those which travel through the grating. FIG. 2 illustrates a reflection grating where the scattered bulk waves of interest are those which are reflected from the grating. Many gratings produce both a transmitted and a reflected bulk wave. The design parameters of the grating are selected to maximize the intensity of the desired scattered wave.

The period S of the grating is approximately equal to the center wavelength of the chirp pulse or a multiple thereof. The scattered bulk wave becomes focused directly below the center of the grating region which scattered the bulk wave. As the period S is increased or decreased, the focus is moved ahead or behind center respectively. As the chirp pulse propagates to the right, so does the focused bulk beam. By choosing the grating wavelength S to be $$S = \frac{V_L}{f_o \cos \alpha}$$

where $V_L$ is the velocity of acoustic bulk waves in the propagation medium 18, $f_o$ is the center frequency of the chirp pulse and $\alpha$ is the grazing angle, the grating scatters the incident acoustic chirp bulk wave into a focused bulk beam having a focus positioned directly below and centered with respect to the region of grating interacting with the chirp pulse to produce the focused bulk beam. As the grating period is increased or decreased, the focus is moved ahead or behind center respectively. The focus is at a distance h from the grating where $$h = \left( \frac{V_L}{V_o \cos \alpha} \frac{f_o}{\Delta f} \right) W$$

$\Delta f$ is the bandwidth of the chirp signal, $V_o$ is the velocity of acoustic bulk waves in the medium below the acoustic grating, which is preferably water, and $W = (V_L \Delta t) \cos \alpha$ is the spatial width of the chirp signal of duration $\Delta t$ on the grating. Accordingly $$h = \left( \frac{V_L^2 f_o}{V_o} \right) \left( \frac{\Delta t}{\Delta f} \right)$$

by substitution, revealing that the focal length h is inversely proportional to the chirp slope, $\Delta f / \Delta t$. The focused spot size w may be found to be $$w = \frac{W}{\Delta f \Delta t \cos^2 \alpha}$$

In FIG. 1, a scan is initiated when a pulse of duration $\Delta t$ is produced by trigger pulse generator 22. Chirp pulse generator 20 forms a chirp pulse having the same time duration $\Delta t$ as the pulse from pulse generator 20 and having a predetermined center frequency $f_o$ and bandwidth $\Delta f$. The chirp pulse is converted by transducer 14 into a bulk wave chirp pulse and it propagates across the substrate 18 grazing the grating 27 and scattering a bulk wave into focus beneath the grating. The focus of the scattered bulk wave travels along plane 30 at a speed $V = V_L \cos \alpha$.

If an acoustic image is desired, the above described launching of a focused acoustic bulk wave is followed in timed sequence by detection of acoustic bulk waves. It is assumed that the focused bulk wave is modulated to a greater or lesser extent at the focal plane by some object with respect to which an acoustic image is desired. Acoustic bulk waves are in general both reflected and transmitted from points along the focal plane 30 and diverge in general from the focus achieved at the focal plane. Reflected bulk waves (echoes) travel towards the grating 27 and can be detected. Transmitted bulk waves diverging from a focus at the focal plane can also be detected, as will be described in further detail subsequently.

Part of the incident echo bulk wave will be scattered by the grating into a bulk wave chirp pulse propagating towards the bulk wave transducer 14. Bulk waves are scattered in other directions also but these components do not reach the transducer 14 and may be neglected. In order to assure that the echo components scattered in other directions do not reach the transducer 14, all nonactive surfaces of scanner 10 are made acoustically absorbing. This is also necessary to prevent spurious reflections in the transmission mode. Transducer 14 converts the echo chirp bulk pulse into an electrical chirp pulse on line 12. The pulse from generator 22 which initiated the launch of the acoustic chirp pulse has been delayed by delay 32 by an amount just sufficient to result in opening of gate 34 as the echo chirp pulse arrives. The returning chirp pulse passes through gate 34 and enters a pulse compression filter 36, the output of which is recorded with recording device 38.

Pulse compression filters are commercially available devices and have the function of compressing a chirp pulse to a single time instant by delaying signal components by an amount proportional to frequency. Delay 40 synchronizes the recording device to the incoming signal by introducing a time delay in the operation of this device which corresponds to the time delay introduced by the pulse compression filter 36. It should be apparent that echo waves originating from positions farther to the right along the focal plane arrive at the pulse compression filter and recording device correspondingly later in time. The echoes from the launch of a single chirp signal thus generate one line of an acoustic image. The other dimension may be scanned by mechanically moving the acoustic scanning apparatus with respect to an object or by any other known method.

During the transmission mode of operation, the acoustic scanning system illustrated in FIG. 2 operates similarly to the system illustrated in FIG. 1 with the exception that the scattered focused bulk wave is reflected from an acoustic grating rather than transmitted through it. Focal plane 30 is shown with respect to an object 42 being scanned. In FIG. 1 the returning chirp pulse was reflected from an object (not shown). In FIG. 2 the returning pulse is transmitted through the object. More significantly, in FIG. 2 the returning pulse is not a chirp pulse and does not interact with a grating. Instead, the transmitted bulk waves are received by a bulk wave transducer 44 and recorded on recording device 38. The trigger pulse generator again is synchronized with the recording device through a suitable delay 32. Bulk wave transducer 44 may have a strip configuration, or comprise an array of strip transducers, aligned either with the X or Y directions. A strip transducer aligned with the X direction, for example, will detect acoustic bulk waves coming from only a particular Y position of the focal plane 30. In the X direction the bulk waves are simultaneously time resolved as described previously.

Figure 3:
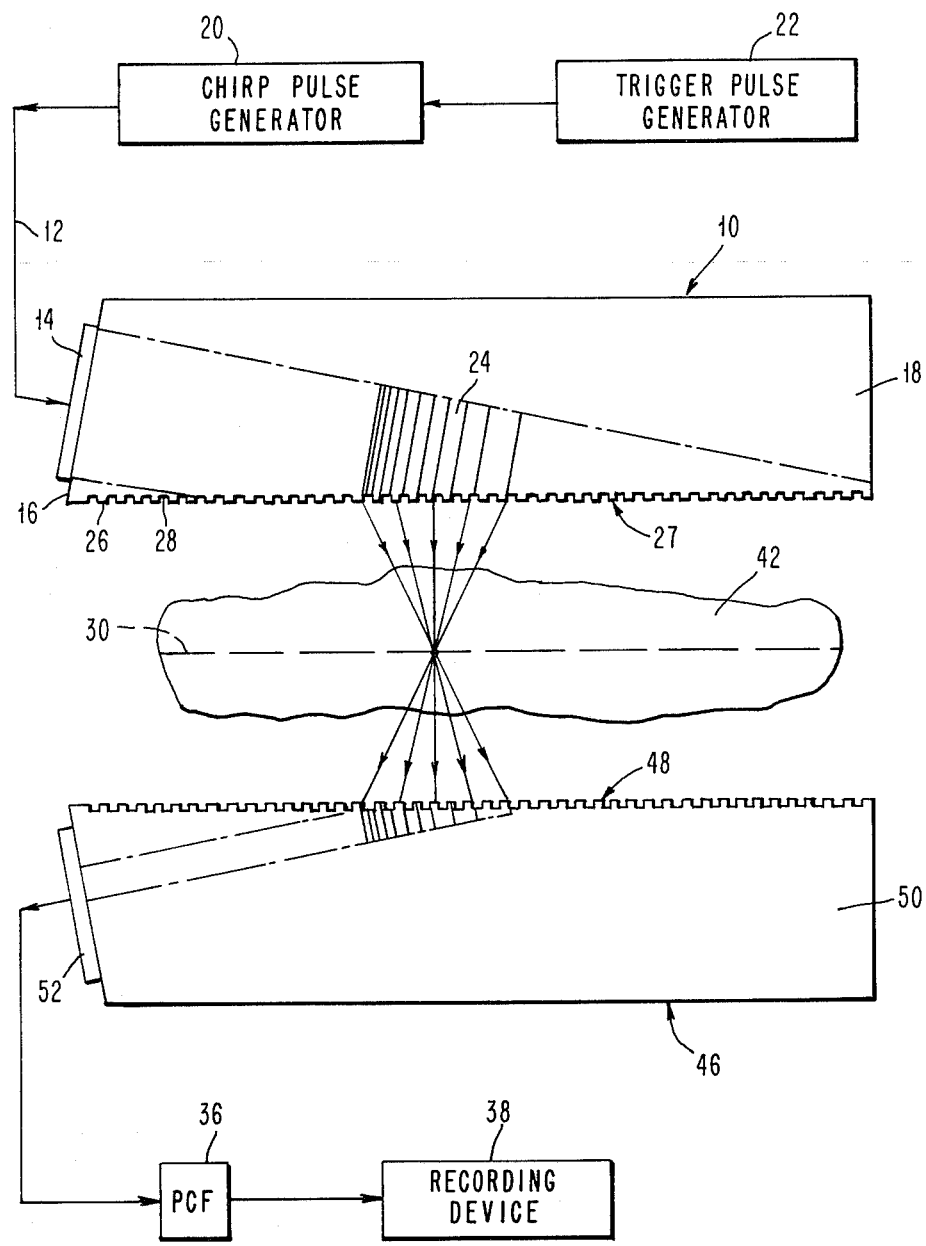
FIG. 3 illustrates a modification of the FIG. 1 embodiment wherein separate grating scanners are used for transmitting and receiving acoustic bulk waves.

It should be apparent that the transmission grating scanner shown in FIG. 1 and the reflection grating scanner shown in FIG. 2 can be substituted for each other. Furthermore, in FIG. 1 it is possible to receive transmitted rather than reflected chirp pulses by positioning a separate grating scanner (reflection or transmission type) below the focal plane and connecting this separate grating scanner directly to a pulse compression filter and recording device. This is shown in FIG. 3. A separate grating scanner 46 (which acts as a receiver) is positioned below the focal plane 30. Transmitted bulk waves diverge from a focus at the focal plane and strike grating 48. Part of the incident bulk waves will be scattered by the grating into a bulk wave chirp pulse propogating through medium 50 towards an output bulk wave transducer 52. Bulk waves are scattered in other directions also but these components do not reach transducer 52 and may be neglected. In order to assure that the components scattered in other directions do not reach transducer 52, all nonactive surfaces of receiver 46 are made acoustically absorbing. Transducer 52 converts the transmitted chirp bulk wave pulse into an electrical chirp pulse, which is compressed by pulse compression filter 36 and recorded by recording device 38 as previously described in reference to FIG. 1. It is also possible in theory to receive reflected bulk acoustic waves also by using a bulk wave strip transducer rather than a grating scanner by creating separate angles of incidence and reflection.

The present invention has been described with respect only to two directions, X and Z. It may have been assumed that the cross section of the grating scanners does not change in the Y direction. This may or may not be true depending upon requirements. If the surface carrying the grating perturbations is cylindrical rather than flat (with the axis of the cylinder being parallel with the X direction), there will simultaneously be a focusing effect in the Y direction. When a reflection type grating scanner is used (FIG. 2), it is possible instead to make the surface 46 cylindrical (the axis of the cylinder being parallel with the X direction) to obtain a focusing effect in the Y direction. It should be apparent furthermore that chirp pulses need not be linear nor launched as planar bulk waves and the acoustic grating need not be uniform in periodicity or amplitude without departing from what we regard as our invention.

Further variations and modifications may also be made without departing from what we regard as our invention. For example, the teachings of our invention may be applied virtually to any embodiment described or suggested in the aforementioned prior art U.S. Pat. No. 4,011,747 by substituting bulk wave scattering of a bulk wave by an acoustic grating as we describe in place of bulk wave scattering of a surface acoustic wave by an acoustic grating as described in the prior art patent. All of the advantages described herein may then be obtained for such other embodiments. Such prior art embodiments modified by the teachings of our invention are also regarded as our invention.

Having thus described our invention, what we claim as new, and desire to secure by Letters Patent is:
1. An acoustic beam scanner, comprising:
an acoustic bulk wave propagation medium;

means for generating a chirp pulse;
transducer means responsive to said chirp pulse for converting said chirp pulse into an acoustic bulk wave chirp pulse propagating through said propagation medium; and
an acoustic grating structure positioned along the propagation path of the acoustic bulk wave chirp pulse such that the acoustic bulk wave chirp pulse intersects the acoustic grating at grazing incidence, the bulk acoustic wave chirp pulse being scattered by the acoustic grating into a focused beam of acoustic bulk waves, the focused beam scanning in a direction parallel with the acoustic grating.

2. A scanner as defined in claim 1 wherein said transducer means comprises an acoustic bulk wave transducer.

3. A scanner as defined in claim 1 wherein said propagation medium comprises fused quartz.

4. A scanner as defined in claim 3 wherein said transducer means comprises $LiNbO_3$.

5. A scanner as defined in claim 1 wherein the position of said acoustic grating structure coincides with a surface of said propagation medium.

6. A scanner as defined in claim 5 wherein said propagation medium is a solid.

7. A scanner as defined in claim 1 wherein said grating comprises an array of obstacles.

8. A scanner as defined in claim 7 wherein said obstacles are elongate grooves parallel with each other.

9. A scanner as defined in claim 7 wherein said grating is on a surface of said propagation medium.

10. A scanner as defined in claim 1 wherein said grating comprises an array of perturbations on a surface of said propagation medium.

11. A scanner as defined in claim 1 wherein said grating is planar.

12. A scanner as defined in claim 1 wherein said chirp pulse is a linear chirp pulse.

13. A scanner as defined in claim 1 wherein said acoustic bulk wave chirp pulse intersects said acoustic grating at an angle of about 10 degrees.

14. A scanner as defined in claim 1 wherein said focused beam is formed by scattered acoustic bulk waves reflected from said grating.

15. A scanner as defined in claim 1 wherein said focused beam is formed by scattered acoustic bulk waves transmitted through said grating.

16. A scanner as defined in claim 1 and further comprising acoustic bulk wave receiver means responsive to acoustic bulk waves arising from said scanning focused beam for converting received bulk waves into an electrical signal.

17. A scanner as defined in claim 16 wherein said receiver means is an acoustic bulk wave transducer.

18. A scanner as defined in claim 17 wherein said transducer is a strip transducer positioned parallel with the scanning direction of the scanning focused beam.

19. Apparatus for converting acoustic bulk waves arising from a scanning focused beam of bulk waves into an electrical signal, comprising:
an acoustic bulk wave propagation medium for receiving acoustic bulk waves arising from a scanning focused beam of bulk waves;
an acoustic grating structure positioned along the propagation path of said acoustic bulk waves such that said acoustic bulk waves intersect the acoustic grating, said acoustic bulk waves being scattered by the acoustic grating into an acoustic bulk wave chirp pulse propagating away from the grating in a predetermined direction;
transducer means responsive to acoustic bulk waves propagating along said predetermined direction for converting said acoustic chirp pulse to an electrical chirp pulse;
pulse compression filter means responsive to said electrical chirp pulse for compressing said electrical chirp pulse; and
means for recording said compressed pulse.

20. Apparatus for generating focused acoustic bulk waves, comprising:
means for generating a chirp pulse;
a propagation medium for acoustic bulk waves;
an array of perturbations located along one surface of the propagation medium; and
transducer means operatively connected to the generating means and the propagation medium for converting the chirp pulse from the generating means into acoustic bulk waves propagating through the medium and intersecting the perturbation array surface of the medium at grazing incidence, the acoustic bulk waves being scattered by the perturbation array into a focused beam of acoustic bulk waves propagating away from the perturbation array surface.

21. Apparatus as defined in claim 20 wherein said focused beam scans in a direction parallel with the perturbation array.

22. Apparatus for converting focused acoustic bulk waves into an electrical signal, comprising:
a propagation medium for receiving acoustic bulk waves diverging from a focus of such waves;
an array of perturbations located along one surface of the propagation medium such that the diverging acoustic bulk waves are incident upon the perturbation array and are scattered thereby;
transducer means operatively connected to the propagation medium for converting acoustic bulk waves scattered by the perturbation array and propagating along substantially the same direction within the medium into a chirp signal; and
pulse compression filter means connected to the transducer means for converting the chirp signal into an electrical signal.

23. Apparatus as defined in claim 22 and further comprising means for recording said electrical signal.

24. Apparatus for scanning an object with focused acoustic bulk waves and for recording the acoustic image of the object, comprising:
means for generating an input chirp pulse;
a propagation medium for transmitting acoustic bulk waves;
an array of perturbations located along one surface of the propagation medium;
input transducer means operatively connected to the generating means and the propagation medium for converting the input chirp pulse from the generating means into acoustic bulk waves propagating through the medium and intersecting the perturbation array surface of the medium at a grazing angle, the acoustic bulk waves being scattered by the perturbation array into a beam of acoustic bulk waves focused within the object, the focused beam scanning across the object and being modulated thereby;

an acoustic bulk wave propagation medium for receiving the acoustic bulk waves modulated by the object;

an array of perturbations located along one surface of the receiving medium such that the acoustic bulk waves modulated by the object are incident upon the perturbation array and are scattered thereby;

output transducer means operatively connected to the receiving medium for converting acoustic bulk waves scattered by the perturbation array and propagating along substantially the same direction within the receiving medium into an output chirp signal;

pulse compression filter means connected to the output transducer means for converting the output chirp signal into an electrical signal; and means connected to the pulse compression filter means for recording the electrical signal therefrom and thereby the acoustic image of the object.

25. Apparatus as defined in claim 24 wherein said propagation medium for transmitting acoustic bulk waves and said propagation medium for receiving the acoustic bulk waves modulated by the object are the same medium.

26. Apparatus as defined in claim 25 wherein said array of perturbations located along one surface of the propagation medium and said array of perturbations located along one surface of the receiving medium are the same array of perturbations.

27. Apparatus as defined in claim 26 wherein said input transducer and said output transducer are the same transducer.

28. Method for generating focused acoustic bulk waves, comprising the steps of:

generating a chirp electrical pulse;

converting the chirp electrical pulse into an acoustic bulk wave chirp pulse;

directing the acoustic bulk wave chirp pulse at grazing incidence onto an acoustic grating, the acoustic bulk wave chirp pulse being scattered thereby into a focused beam of acoustic bulk waves.

29. The method of claim 28 wherein said focused beam scans in a direction parallel with said grating.

30. Method for converting diverging acoustic bulk waves arising from a scanning focused beam of bulk waves into an electrical signal, comprising the steps of:

scattering the diverging acoustic bulk waves from an acoustic grating;

converting the scattered acoustic bulk waves which are propagating along substantially the same direction into an electrical chirp pulse; and pulse compression filtering the electrical chirp pulse into an electrical signal.

31. The method of claim 30 and further comprising the step of recording said electrical signal.

* * * * *